US008613741B1

(12) United States Patent
Jones et al.

(10) Patent No.: US 8,613,741 B1
(45) Date of Patent: Dec. 24, 2013

(54) VOLTAGE BUCKING CIRCUIT FOR DRIVING FLASHLAMP-PUMPED LASERS FOR TREATING SKIN

(75) Inventors: Christopher J. Jones, Leicester, MA (US); James C. Hsia, Weston, MA (US); Scott Mogren, Holliston, MA (US)

(73) Assignee: Candela Corporation, Wayland, MA (US)

( * ) Notice: Subject to any disclaimer, the term of this patent is extended or adjusted under 35 U.S.C. 154(b) by 1699 days.

(21) Appl. No.: 11/870,933

(22) Filed: Oct. 11, 2007

Related U.S. Application Data

(60) Provisional application No. 60/850,755, filed on Oct. 11, 2006.

(51) Int. Cl.
*A61B 18/18* (2006.01)

(52) U.S. Cl.
USPC .......................................................... 606/9

(58) Field of Classification Search
USPC .............................. 606/9–12; 607/80, 88–90; 372/29.011–29.021, 30–31, 372/38.01–38.08
See application file for complete search history.

(56) References Cited

U.S. PATENT DOCUMENTS

| | | | |
|---|---|---|---|
| 3,914,648 A | 10/1975 | Friedman et al. | 315/241 P |
| 3,992,684 A | 11/1976 | Patrick et al. | 331/94.5 |
| 4,150,342 A | 4/1979 | Johnston, Jr. et al. | 331/94.5 S |
| 4,398,129 A | 8/1983 | Logan | 315/208 |
| 4,469,991 A | 9/1984 | McAllister | 315/246 |
| 4,611,270 A | 9/1986 | Klauminzer et al. | 364/183 |
| 4,627,063 A | 12/1986 | Hosokawa | 372/38 |
| 4,823,354 A | 4/1989 | Znotins et al. | 372/57 |
| 4,829,262 A | 5/1989 | Furumoto | 330/4.3 |
| 4,891,817 A | 1/1990 | Duarte | 372/54 |
| 5,023,865 A | 6/1991 | Grant et al. | 370/3 |
| 5,054,028 A | 10/1991 | Esherick et al. | 372/32 |
| 5,196,766 A | 3/1993 | Beggs | 315/241 |
| 5,255,274 A | 10/1993 | Wysocki et al. | 372/26 |
| 5,255,277 A | 10/1993 | Carvalho | 372/38 |
| 5,287,380 A | 2/1994 | Hsia | 372/69 |
| 5,315,607 A | 5/1994 | Nielsen | 372/38 |
| 5,373,515 A | 12/1994 | Wakabayashi et al. | 372/20 |
| 5,497,051 A | 3/1996 | Langhans et al. | 315/200 |

(Continued)

OTHER PUBLICATIONS http://www.thefreedictionary.com/system, definition of the term system, retrieved May 18, 2012.*

(Continued)

*Primary Examiner* — Ryan Severson
*Assistant Examiner* — David Eastwood
(74) *Attorney, Agent, or Firm* — Proskauer Rose LLP

(57) ABSTRACT

Described is a device for driving a dermatological laser. The system includes a first diode, an inductor, a switch, and a photodetector. A first end of the inductor is coupled to an end of the first diode, and a second end of the inductor is coupled to a flashlamp. An electrical control of the switch is coupled to a control system, a first end of the switch is coupled to a power source, and a second end of the switch is coupled to the first end of the inductor and the end of the first diode. The photodetector is adapted to measure at least one of output energy or output power of a laser medium pumped by the flashlamp. The photodetector is in communication with the control system for modulating a flashlamp that drives current to maintain a predetermined value of the measured output energy or output power.

19 Claims, 4 Drawing Sheets

(56) References Cited

U.S. PATENT DOCUMENTS

| | | | |
|---|---|---|---|
| 5,585,698 A | 12/1996 | Langhans et al. | 315/200 |
| 5,598,426 A | 1/1997 | Hsia et al. | 372/53 |
| 5,624,435 A | 4/1997 | Furumoto et al. | 606/10 |
| 5,692,004 A | 11/1997 | Greene | 372/69 |
| 5,735,844 A | 4/1998 | Anderson et al. | 606/9 |
| 5,739,643 A | 4/1998 | Usui | 315/241 |
| 5,746,735 A | 5/1998 | Furumoto et al. | 606/9 |
| 5,843,072 A | 12/1998 | Furumoto et al. | 606/9 |
| 5,871,479 A | 2/1999 | Furumoto et al. | 606/9 |
| 5,911,718 A | 6/1999 | Yarborough et al. | 606/9 |
| 5,921,981 A | 7/1999 | Bahmanyar et al. | 606/4 |
| 6,045,548 A | 4/2000 | Furumoto | 606/9 |
| 6,050,990 A | 4/2000 | Tankovich et al. | 606/9 |
| 6,130,900 A | 10/2000 | Black et al. | 372/25 |
| 6,228,075 B1 | 5/2001 | Furumoto | 606/9 |
| 6,273,883 B1 | 8/2001 | Furumoto | 606/9 |
| 6,364,872 B1 | 4/2002 | Hsia et al. | 606/9 |
| 6,512,782 B1 * | 1/2003 | Hsia et al. | 372/25 |
| 6,547,781 B1 | 4/2003 | Furumoto | 606/12 |
| 6,610,052 B2 * | 8/2003 | Furumoto | 606/9 |
| 6,632,218 B1 | 10/2003 | Furumoto et al. | 606/9 |
| 6,676,655 B2 | 1/2004 | McDaniel | 606/9 |
| 6,829,260 B2 | 12/2004 | Hsia et al. | 372/25 |
| 7,274,155 B2 | 9/2007 | Inochkin et al. | 315/247 |
| 7,465,307 B2 | 12/2008 | Connors et al. | 606/88 |
| 2001/0009997 A1 * | 7/2001 | Pope et al. | 606/9 |
| 2002/0014855 A1 * | 2/2002 | Rizoiu et al. | 315/200 R |
| 2002/0016587 A1 * | 2/2002 | Furumoto | 606/7 |
| 2002/0049433 A1 * | 4/2002 | Furumoto et al. | 606/9 |
| 2002/0149326 A1 * | 10/2002 | Inochkin et al. | 315/242 |
| 2003/0057875 A1 * | 3/2003 | Inochkin et al. | 315/224 |
| 2003/0108078 A1 * | 6/2003 | McCarthy et al. | 372/69 |
| 2003/0144713 A1 | 7/2003 | Furumoto | 607/89 |
| 2003/0227953 A1 * | 12/2003 | Hsia et al. | 372/53 |
| 2003/0231678 A1 * | 12/2003 | Stuart | 372/38.06 |
| 2005/0049658 A1 * | 3/2005 | Connors et al. | 607/88 |
| 2007/0030612 A1 * | 2/2007 | Kamath | 361/82 |

OTHER PUBLICATIONS

Miller et al., "5-J 1.8-μsec pulse 10 pps dye laser for combustion applications," Applied Optics, 21, No. 10, May 15, 1982, pp. 1764-1766.

Sierra, R., "Flashlamp-excited dye lasers achieve new performance levels," Laser Focus, 24, No. 4, Apr. 1988, pp. 77, 78, 80, 82, 84, 86, 88, 90 and 91.

\* cited by examiner

VOLTAGE BUCKING CIRCUIT FOR DRIVING FLASHLAMP-PUMPED LASERS FOR TREATING SKIN

CROSS-REFERENCE TO RELATED APPLICATION

This application claims the benefit of and priority to U.S. Provisional Application Ser. No. 60/850,755 filed Oct. 11, 2006, which is owned by the assignee of the instant application and the disclosure of which is incorporated herein by reference in its entirety.

FIELD OF THE INVENTION

The invention relates generally to a dermatological laser. In particular, the invention relates to a device that regulates the flashlamp current using a voltage bucking circuit configuration and a photodetector to measure the output of a laser. The circuit includes an inductor coupled to a diode and a switch for driving a flashlamp-pumped laser.

BACKGROUND OF THE INVENTION

Lasers are widely used in dermatological applications such as hair removal, removal of pigmented lesions, tattoos, vascular lesions, wrinkles, acne, and skin tightening. These and similar applications are effected by heating only a small structure in the skin to a temperature above that which initiates a healing process that removes or replaces the small structure. These laser treatments are typically based on selective targeting of a chromophore in the skin by an appropriate choice of wavelength and pulse duration of the laser light. For example, the blood vessels in vascular lesions are irradiated with a color of light, usually yellow, that is well absorbed by the blood. The absorbed light heats the blood and the blood then heats the vessel walls. Lasers that are able to emit pulses of high peak power work well because the heat builds up in the vessel walls faster than it can be conducted through the wall to the surrounding skin tissue. Most of the heat is confined to the vessel and so it is damaged while most of the surrounding tissue is spared. Treatment pulse durations of several milliseconds are often most effective but effective pulse durations can range from a hundred of microseconds to hundreds of milliseconds. Some lasers can be pumped by flashlamps to get the large pulse energies required for creating the desired thermal profile in the skin.

Several lasers are well suited for use in medical applications. Some high power, pulsed lasers are the preferred instruments for treating certain dermatological conditions. Many of these lasers can be pumped with flashlamps. Flashlamps offer an economical means of delivering several megawatts of pump power in short duration pulses. Examples of flashlamp pumped medical lasers are dye lasers and solid state lasers such as Alexandrite, Ruby and Nd:YAG. Some flashlamp pumped lasers are most efficient when the pulse duration of the laser is shorter than the desired treatment pulse duration for heating the tissue target. In these cases, the laser can be made to emit a long train of short sub-pulses that are spaced in time to produce an effective pulse duration that equals the desired treatment pulse duration.

Some driver circuits for flashlamps use a series of energy storage capacitors that can be discharged sequentially through the flashlamp to generate a train of laser sub-pulses. Each capacitor can be individually charged to different voltages so that the magnitude of the flashlamp current in the sequentially produced flashlamp sub-pulses can be made to increase over that of the previous sub-pulse. The maximum number of sub-pulses in a driving configuration, however, using a series of energy storage capacitors is limited to the number of capacitors. Another disadvantage is that, in practice, the energy delivered in each laser sub-pulse needs to be adjusted individually for the desired output energy. This system becomes complex and difficult to calibrate for a large numbers of sub-pulses.

In other driver circuits, an IGBT is used to connect an energy storage capacitor to the flashlamp. The amplitude of the flashlamp current is determined by the capacitor voltage and the impedance of the flashlamp. The problem with this circuit is that the capacitor voltage drops during the pulse. Therefore, the flashlamp current and hence the peak power of the resultant laser pulse both decrease during the pulse. When used in a multiple sub-pulse mode, each laser sub-pulse has a lower peak power than the previous sub-pulse. At some point in time the laser gain can fall below threshold and lasing ceases. This is a problem for lasers, such as pulsed dye lasers, that suffer a drop in the laser efficiency during a single pulse and in each subsequent sub-pulses due to thermal and other degradations in the lasing medium.

SUMMARY OF THE INVENTION

The invention, in various embodiments, features a dermatological laser. The laser can be driven using a voltage bucking configuration, which can include an inductor coupled to a diode and a switch.

In one aspect, the invention features a system for driving a dermatological laser. The system includes a first diode, an inductor, a switch, and a photodetector. A first end of the inductor is coupled to an end of the first diode, and a second end of the inductor is coupled to a flashlamp. An electrical control of the switch is coupled to a control system. A first end of the switch is coupled to a power source, and a second end of the switch is coupled to the first end of the inductor and the end of the first diode. The photodetector is adapted to measure at least one of output energy or output power of a laser medium pumped by the flashlamp. The photodetector is in communication with the control system for modulating a flashlamp that drives current to maintain a predetermined value of the measured output energy or output power.

In another aspect, the invention features a method for driving a dermatological laser. The method includes supplying a voltage to a first end of a switch. The method also includes turning on the switch for supplying a first current through the switch and an inductor. A first end of the inductor is coupled to an end of the switch. A second end of the inductor is coupled to a flashlamp. The first current drives the flashlamp. The method also includes turning off the switch for supplying a second current through a diode and the inductor. The first end of the inductor is coupled to an end of the diode. The inductor drives the second current from a stored magnetic field. The second current drives the flashlamp. The method also includes measuring, using a photodetector, at least one of output energy or output power of a laser medium pumped by the flashlamp. The photodetector is in communication with the control system for modulating a flashlamp driving current to maintain a predetermined value of the measured output energy or output power.

In yet a further aspect, the invention features a system for driving a flashlamp for treating skin including a first diode, an inductor, and an insulated gate bipolar transistor (IGBT). A first end of the inductor is coupled to a cathode end of the first diode, and a second end of the inductor is coupled to a flashlamp. A gate of the IGBT is coupled to a control system.

A first end of the IGBT is coupled to a power supply, and a second end of the IGBT is coupled to the first end of the inductor and the cathode of the first diode. When the control system drives the gate of the IGBT high, a first current is supplied through the IGBT and the inductor for driving the flashlamp. When the control system drives the gate of the IGBT low, a second current is supplied through the first diode and the inductor. The inductor drives the second current from a stored magnetic field. The second current drives the flashlamp.

In other examples, any of the aspects above or any apparatus or method described herein can include one or more of the following features. In various embodiments, the system can further include a second diode coupling the second end of the inductor to the flashlamp. In one embodiment, the system can further include a snubber circuit coupled to the first end of the inductor. The snubber circuit can supply a current to the inductor when the control system drives the electrical control to turn off the switch. The flashlamp can include one or more separate flashlamps connected in series. The switch can be a transistor. The transistor can be an insulated gate bipolar transistor (IGBT). The electrical control can be a gate of the transistor.

In various embodiments, the system can further include a laser medium adapted to receive one or more flashlamp light pulses generated by the flashlamp for producing an output laser beam. The output laser beam can include one or more laser radiation pulses corresponding to the one or more flashlamp light pulses. The system can be used to generate a laser beam with constant output power, a rising output power, or a decreasing output power. The system can be used to generate a series of laser sub-pulses such that each sub-pulse contains the same energy, increasing energy, or decreasing energy.

In some embodiments, the control system can be adapted to adjust an amplitude of the flashlamp driving current in coordination with a changing lasing efficiency of the flashlamp-pumped laser. The flashlamp-pumped laser can be a flashlamp-pumped dye laser. The flashlamp-pumped dye laser can include a liquid dye laser medium adapted to receive one or more flashlamp light pulses generated by the flashlamp for producing an output laser beam, which includes a laser treatment pulse. The laser treatment pulse can include one or more laser radiation sub-pulses corresponding to the one or more flashlamp light pulses. The laser treatment pulse can be initiated by a trigger signal. The trigger signal can initiate an emission of the laser treatment pulse at a repetition rate up to about 2 pulses per second. Each laser treatment pulse can have an energy greater than about 1 Joule. The laser treatment pulse can include a single laser radiation sub-pulse of greater than 100 microseconds duration. The single laser radiation sub-pulse can be one of: substantially constant output power, rising output power, or decreasing output power. The laser treatment pulse can include between two and eight laser radiation sub-pulses each being at least about 10 microseconds duration. The laser treatment pulse can be spaced out over a time of about 400 microseconds to about 40 milliseconds. The energy in each laser radiation sub-pulse can be substantially equal. In some embodiments, the maximum number of laser radiation sub-pulses can be greater than eight. Each laser radiation sub-pulse of the laser treatment pulse can have a duration of at least about 10 microseconds. The laser treatment pulse can be spaced out over a time of about 400 microseconds to about 40 milliseconds. The energy in each laser radiation sub-pulse can be substantially equal. Each laser treatment pulse can have a pulse duration of 100 microseconds to 100 milliseconds. In another embodiment, the laser radiation sub-pulses can be emitted continuously, spaced in time, to form a quasi-CW laser treatment beam. The quasi-CW laser treatment beam can be scanned over the treatment area. The initiation and termination of the quasi-CW laser treatment beam can be controlled.

In some embodiments, the system can further include a wavelength sensor and a tuning system in communication with the wavelength sensor for varying a wavelength of the one or more laser radiation pulses. The wavelength of the one or more laser radiation pulses can be between about 580 nanometers to about 610 nanometers. The wavelength of the one or more laser radiation pulses can be between about 590 nanometers to about 600 nanometers. The system can further include a flexible aiming device for directing the output beam to a treatment region. The system can further include an aiming device for providing an aiming beam to align the output beam with a treatment region. The aiming beam can include green light. The system can further include a cryogen spray device for cooling a treatment region prior to irradiation.

In some embodiments, the system can further include a skin diagnostic device for varying the power, energy, and/or pulse duration of the flashlamp and the resultant laser output in response to the measured such skin parameters such as reflectivity of the skin, the temperature of the skin, or changes in these parameters as the laser radiation is applied to the skin indicating that a desired treatment end point has been reached.

In some embodiments, the method can further include supplying a current, using a snubber circuit coupled to the first end of the inductor, to the inductor when the control system turns the switch off. The method can further include producing, using a laser medium, an output laser beam based on one or more flashlamp light pulses generated by the flashlamp. The output laser beam can include one or more laser radiation pulses corresponding to the one or more flashlamp light pulses. The method can further include adjusting, using the control system, an amplitude of the flashlamp driving current in coordination with a changing lasing efficiency of the flashlamp-pumped laser medium. The method can further include varying, using a tuning system in communication with a wavelength sensor, a wavelength of the one or more laser radiation pulses. The method can further include directing, using a flexible aiming device, the output beam to a target.

Advantages of the invention can include one or more of the following. The number of sub-pulses capable of being produced by the flashlamp driver circuit is not limited by, for example, the number of capacitors. The driving circuit configuration is also simple and compact. In addition, the high level of current modulation obviates the need for rapid dye replacement in a dye-laser system. Furthermore, an IGBT can be operated at a reasonable frequency so that the switching losses are moderate. The system can also be operated in a quasi-CW mode. In addition, the present invention allows for more efficient and accurate control of the output laser power. Furthermore, control of the output laser power can be based in real-time.

The present invention can also be advantageously used to drive the flashlamp used in devices (e.g., intense pulse light (IPL) devices) where the flashlamp radiation is used directly to treat the skin after the lamp's emission spectrum has been modified by spectral filters. For example, the present invention can be used in IPL devices to maintain a constant flashlamp current, such that the output spectrum of the lamp can be held constant.

The details of one or more examples are set forth in the accompanying drawings and the description below. Further features, aspects, and advantages of the invention will become apparent from the description, the drawings, and the claims. The drawings are not necessarily to scale, emphasis instead generally being placed upon illustrating the principles of the invention.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DESCRIPTION OF THE INVENTION

Lasers and other light sources are often used for the treatment of skin disorders and to improve the appearance of the skin. The heat produced by the light energy can modify structures within the skin and beneath the skin. Typical applications can include, for example, removal of hair, pigmented lesions, tattoos, vascular lesions, wrinkles, acne, skin tightening, and/or the like. Lasers are often the preferred light source because a laser beam has a narrower wavelength bandwidth than light from other sources. In addition, lasers can be made with much shorter pulse durations than other light sources, thereby maximizing the temporal selectivity of the targeted structure.

Figure 1:
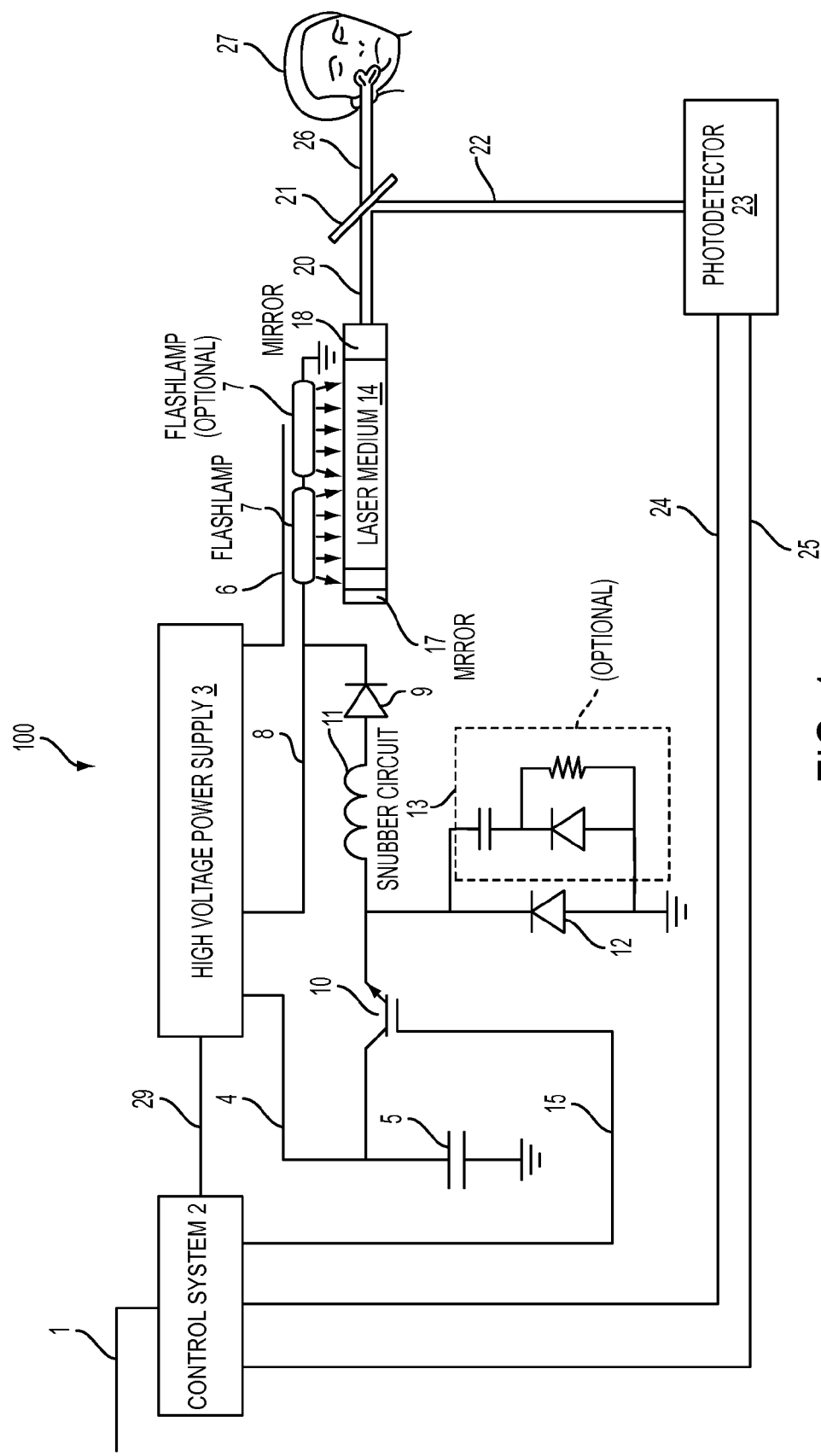
FIG. 1 is a schematic drawing of an electrical circuit capable of driving one or more flashlamps to pump a laser.

FIG. 1 illustrates one embodiment of a system 100 including an electrical circuit capable of driving one or more flashlamps to pump a laser. A flashlamp 7 is driven with an insulated gate bipolar transistor (IGBT) 10, an inductor 11 and a diode 12 connected in a voltage bucking configuration. The flashlamp 7 can be a single flashlamp or more than one flashlamp connected in series. The IGBT 10 can be operated in a high frequency switching mode, and the inductor 11 and diode 12 can form a parallel circuit that continues to provide the flashlamp 7 current during an off state of the IGBT 10. System 100 combines the flexibility and simplicity of an IGBT with the ability to increase the current during a single long pulse or a series of sequentially produced flashlamp pulses even though the voltage on an energy storage capacitor 5 decreases during the pulse. The use of a calibrated photodetector 23 to monitor the laser output 20 allows the system 100 to self-adjust the flashlamp output so that the laser power and/or pulse energy can be controlled in real-time. The timing, power and energy of each sub-pulse can be controlled independently of the other sub-pulses. The laser output power can also be predetermined to either increase, decrease, or remain essentially constant during the pulse or series of sub-pulses.

Referring to system 100, the control system 2 can signal the high voltage power supply 3 to raise the voltage on the simmer output line 8. Little or no current flows because the resistance of the flashlamp 7 is high and the isolation diode 9 prevents current from flowing into the rest of the high voltage system. The high voltage power supply 3 can send a high voltage spike to the simmer start electrode 6 to ionize the gas (e.g., xenon and/or the like) inside the flashlamp 7 in order to lower its electrical resistance. Once the gas is ionized, a constant DC simmer current of about 0.1 amperes, for example, passes through the simmer output line 8 to the flashlamp 7 thereby maintaining the ionic state of the gas. The control system 2 can also send a signal to the high voltage power supply 3 through the inhibit line 29 to enable the high voltage output 4 to charge capacitor 5 to an operating voltage, which can store up to about several thousand Joules of electrical energy.

In another embodiment, the circuit illustrated FIG. 1 can be implemented using the opposite polarity. The voltage polarity on the high voltage line 4, energy storage capacitor 5, and the simmer output line 8 can be negative as long as the IGBT 10 and both diodes 9 and 12, and the snubber 13 are connected in the reverse directions of those shown in FIG. 1.

Returning to FIG. 1, upon initiation of a trigger input 1 by a laser operator (not shown), the control system 2 can drive an insulated gate bipolar transistor (IGBT) gate control line 15 high in order to turn on a IGBT 10. Current begins to flow through the inductor 11, the isolation diode 9 and the flashlamp 7. When the IGBT 10 is turned off, the energy that has been stored in the magnetic field of the inductor 11 can supply the flashlamp 7 with current by the conduction of current through the flashlamp 7. This drives the voltage on the cathode of diode 12 negative so that the diode 12 will begin conducting and can complete the current path. Since the diode 12 is off and had been reversed biased, there can be a finite period of delay before conduction can begin. An optional snubber 13 can be connected across the diode 12 in order to minimize the negative swing which can stress and damage the open IGBT 10 if the maximum $V_{ce}$ is exceeded. The snubber 13 can provide current to the flashlamp 7 so that the cathode of diode 12 will not be driven excessively negative before the diode 12 turns on.

Figure 2:
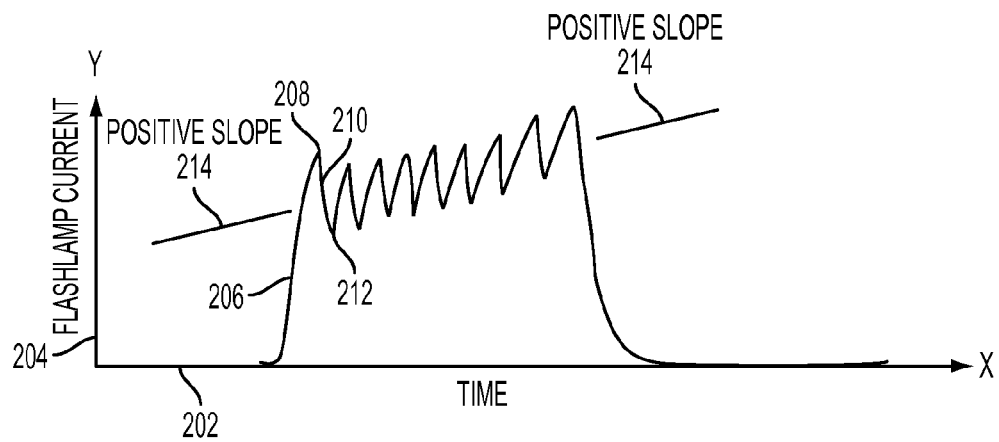
FIG. 2 is a graph of a waveform of the flashlamp current.

FIG. 2 illustrates an example waveform of the current through flashlamp 7 during a complete laser treatment pulse of about 450 microseconds duration. The x-axis 202 indicates time and the y-axis 204 indicates flashlamp current. The pulse can begin with the turn-on of the IGBT 10. Therefore, the initial rise in current 206 is the current that is passing through the IGBT 10. The rate of rise of the current 206 is limited by the inductor 11. As the current rises, some energy is stored in the inductor 11. When the IGBT 10 current is terminated at 208, snubber current (if a snubber 13 is used) can begin to flow for a few microseconds until the diode current 210 from diode 12 begins to flow. The IGBT 10 is turned on again at 212. Thus, the waveform of the flashlamp current includes an alternating sequence of rising IGBT current and falling diode current with possible periods of short snubber current during each transition from IGBT current to diode current. All together, the IGBT 10 was turned on nine times during the pulse in FIG. 2, during which there is a positive slope 214 to the average peak flashlamp current.

When the IGBT 10 is initially turned on and flashlamp current begins to rise, the flashlamp can begin to emit a significant amount of optical radiation. Returning to FIG. 1, some of the radiation generated by the flashlamp 7 can be absorbed by the laser medium 14. In one embodiment, the laser medium 14 can be a solution of laser dye which is made to flow through a long glass dye cell. The flashlamp 7 can be situated next to and in parallel with the dye cell. One or both of the flashlamp 7 and the dye cell can be surrounded by a reflective material (not shown) so that much of the optical radiation generated by the flashlamp 7 can be passed into the laser medium 14 to provide gain for lasing. Two mirrors 17 and 18 can form the laser resonator cavity.

Once the rate of excitation exceeds the threshold for lasing, a laser output beam 20 can be generated. The power that is needed to reach the threshold for lasing does not contribute to the energy of the laser beam 20. Therefore, the amount of wasted energy is proportional to the duration of a flashlamp pulse. The output energy may be only a few percent of the electrical input energy. Lasers can be pumped with short, high peak-power pulses where the rate of pumping can be made much greater than the threshold power in order to improve the efficiency that is the ratio of output energy to input energy.

Figure 3:
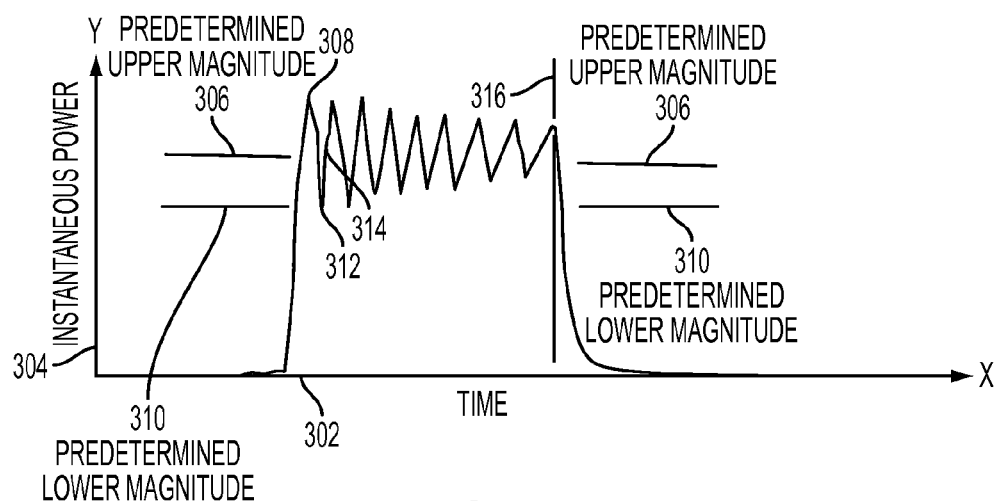
FIG. 3 is a graph of a waveform of the laser beam power.

FIG. 3 illustrates an example graph of the power of the laser beam 20 in a 450 microsecond laser treatment pulse. The x-axis 302 is time and the y-axis 304 is the instantaneous power of the laser output beam 20. As the laser beam 20 passes through a beam splitter 21, a small fraction of the laser beam 20 can be reflected into a laser energy and power detector 23. When the laser power of the reflected beam 22 reaches a predetermined upper magnitude 306, the IGBT gate control line 15 can be brought low in order to turn off the IGBT 10. The laser power can overshoot 308 due to unavoidable switching and propagation delays in the electronics. As explained above, the flashlamp current can drop during the diode conduction phase of the flashlamp current waveform. The laser output power can similarly follow the drop in the flashlamp output. When the output power drops below a predetermined lower magnitude 310, the IGBT 10 can be turned on again. The effect of the electronic delays can similarly be seen in the waveform of the laser power. It falls below the desired magnitude to 312 where the IGBT current begins to flow again and the flashlamp current begins to rise leading to increasing laser output power 314. This modulating of the flashlamp current, and hence the laser power, can continue until a predetermined output energy is reached at 316, at which time the control system can turn off the IGBT 10. The output of the flashlamp 7 drops to zero as the current through diode 12 drains the energy stored in the inductor 11 into the flashlamp 7. During the fall of the flashlamp current, the flashlamp radiation can diminish to a point where the excitation of the laser medium 14 is no longer sufficient to support laser action. The frequency of the modulation can decrease during the pulse, because the voltage on the energy storage capacitor 5 can drop during the pulse and because higher current may be required near the end of the pulse. The laser beam 26 that passes through the beam splitter can be aimed at a skin lesion, such as a vascular lesion, of a patient 27 being treated. A flexible beam delivery system, such as, for example, an optical fiber, can be used to direct the laser beam 26 to the skin lesion of a patient 27.

The skin lesion can be cooled in order to reduce the incidence of epidermal damage. There are several methods of cooling the skin in applications like this. One particularly effective method is using a cryogen spray device to spray a cryogenic fluid such as the non-chlorinated, hydrofluorocarbon 134a on the treatment spot. This material can evaporate quickly and can lower the temperature of the superficial layers of the skin, thereby protecting the superficial layers from thermal injury. A typical spray volume can be about 100 micro-liters and, usually, the fluid can be applied a few tens of milliseconds before the laser radiation is emitted. The spray can also be applied between sub-pulses and at the end of the pulse.

FIG. 2 illustrates that the IGBT 10 was turned on a total of nine times during the pulse. FIG. 2 also illustrates that the peak current can tend to rise during the pulse. This is because the efficiency of a laser medium (such as a dye laser) can drop during the pulse. The efficiency can be defined as the ratio of the output power of the laser beam to the electrical input power to the flashlamp. The flashlamp input needs to rise in order to maintain the level profile of the laser power as indicated in FIG. 3. The drop in efficiency can have several causes. For dye lasers, the radiation from the flashlamp 7 can both heat the dye solution and degrade some of the dye molecules. The heat is deposited mostly at the circumferential surface of the column of dye. This can lead to a gradient in the refractive index of the dye solution over the radial cross-section of the column of dye. The turbulent nature of the flowing dye can disturb the index gradient thereby creating a chaotic variation in the refractive index throughout the laser medium, leading to increased scatter of the laser beam. This tends to spoil the quality of the resonator cavity, which introduces additional losses in the laser cavity. This effect is cumulative during the pulse, contributing to the continuing decrease in laser efficiency during the pulse.

One way to minimize the scatter is to slow the flow rate in order to eliminate turbulence and/or to stop the flow of the dye a short time prior to energizing the flashlamp. Because the dye is still or at least not turbulent, the index gradient can be more stable and a thermally induced positive lens can therefore form in the column of dye which can tend to increase the resonator stability. This can help to offset the effect of the degraded dye molecules mentioned above.

Figure 4:
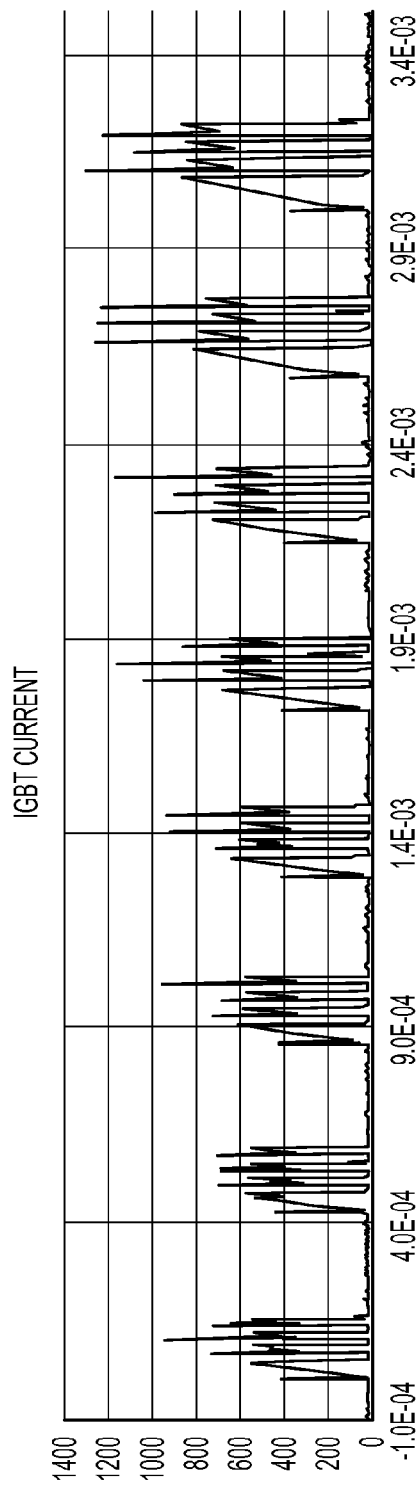
FIG. 4 is a graph of a waveform of the IGBT current.
Figure 5:
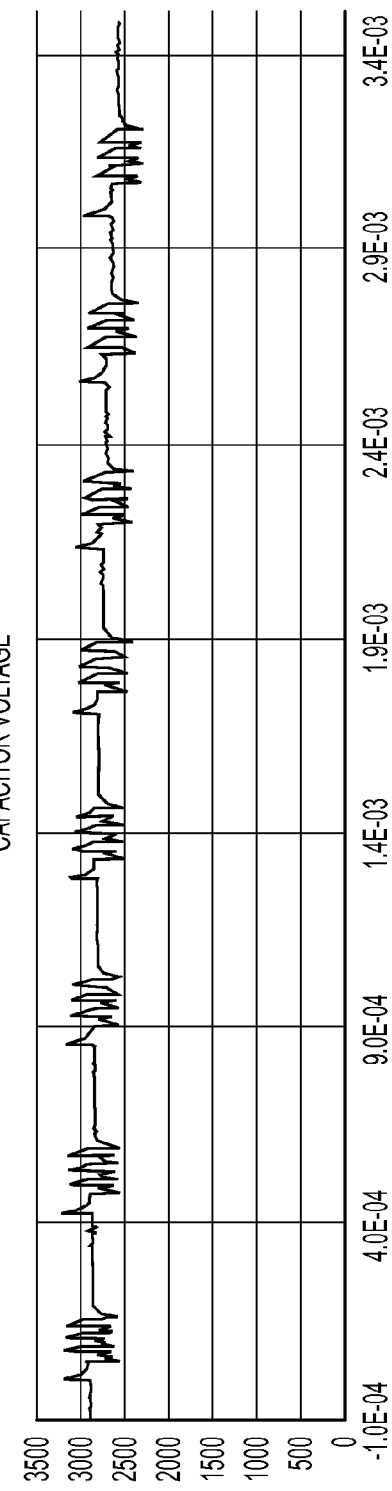
FIG. 5 is a graph of a waveform of the capacitor voltage.

FIG. 4 illustrates an example waveform of an IGBT current for a 3.5 millisecond laser treatment pulse that includes eight sub-pulses. The x-axis is time in seconds and the y-axis is electrical current in amperes. In this example, the IGBT 10 has been turned-on four times in each of the sub-pulses. The peak current of the series of sub-pulses rises over the 3.5 millisecond duration of the pulse so that the peak laser power (not shown) of each of the sub-pulses was essentially constant throughout the pulse. FIG. 5 illustrates the voltage on the capacitor 5 during the same laser treatment pulse as illustrated in FIG. 4. The x-axis is the same as in FIG. 4 and the y-axis is in volts. In this example, the initial voltage is 2,900 volts and the final voltage is 2,600 volts. The flashlamp current, therefore, can be made to increase even though the voltage on the energy storage capacitor 5 drops during the pulse.

Figure 6:
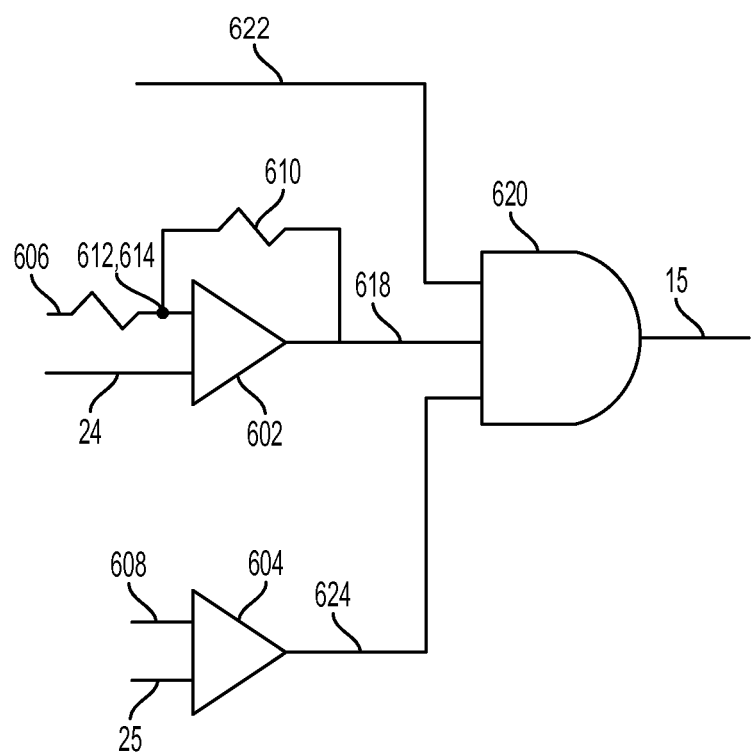
FIG. 6 is a schematic drawing for initiating laser pulses and controlling the peak power and pulse energy.

FIG. 6 illustrates an example scheme for initiating laser pulses and controlling the peak power and pulse energy. The laser energy and power detector 23 can generate two calibrated voltage signals 24 and 25. The laser power signal 24 can be made proportional to the instantaneous power of the laser beam, and the laser energy signal 25 can be made proportional to the accumulated laser energy following the initiation of the laser pulse or subpulse. In FIG. 6, signals 24 and 25 are compared at 602 and 604 to two reference voltage signals: Power Ref 606 and Energy Ref 608, respectively. Power Ref signal 606 can be modulated slightly by a feedback resistor 610 in order to introduce hysteresis. The hysteresis can be set to obtain a suitable frequency range of modulation. Therefore, Upper Power Ref 612 and Lower Power Ref 614 signals are generated depending on the logic level of signal "NOT laser power" 618. The IGBT gate drive 15 can be controlled by the output of an AND logic gate 620. In this example, there are three inputs to the AND gate 620: "pulse enable" 622, "NOT laser power" 618, and "NOT laser energy" 624. The rising edge of "pulse enable" 622 initiates the pulse and can be held high until the pulse is terminated. The "NOT laser power" 618 is always high until the laser power signal 24 rises above the Upper Power Ref voltage 612 and remains low until the laser power signal 24 drops below the Lower Power Ref voltage 614. The "NOT laser energy"

624 is always high until the laser energy signal 25 rises above the Energy Ref voltage 608 and then remains low until reset at a later time.

Referring to FIG. 6, a pulse or sub-pulse can be initiated by raising the "pulse enable" 622 to the high state. The output of the AND gate 620 then goes high, signaling the IGBT drive 15 to turn on the IGBT 10. The current through flashlamp 7 rises, and when the pumping exceeds a threshold level, lasing can begin. Lasing power rises following the rising flashlamp current. The laser power signal 24 can rise proportionately, and when it surpasses the Upper Power Ref voltage 612, the IGBT 10 is turned off. Current through diode 12 commences, wherein the current can subsequently drop when the laser power drops similarly. When the laser power signal 24 goes below the Lower Power Ref voltage 614, the IGBT 10 can be turned on again. The laser output 20 begins to rise again, and in this way, the laser power fluctuates about an average peak power level. During the lasing pulse, the laser energy signal 25 rises proportionally with the accumulation of energy in the current laser pulse. When this signal exceeds the Energy Ref voltage 608, the "NOT laser energy" input 624 to the AND gate 620 goes low, the AND gate output goes low and the IGBT 10 is shut off. The "laser enable" signal 622 and the laser energy signal 25 can both be reset to low and the laser waits for the next "laser enable" signal 622 to begin a new pulse or sub-pulse. A pulse that includes a series of equal sub-pulses can be produced by setting both the Energy Ref 608 and Power Ref 606 to appropriate levels and then sequentially initiating each of the sub-pulses by raising the level of the "laser enable" 622 to the high state for each sub-pulse. Alternatively, the level of either or both the Energy Ref 608 and/or Power Ref 606 can be changed between sub-pulses so that the peak power and energy of each sub-pulse can differ from the other sub-pulses.

The circuit as described above is capable of maintaining a relatively constant laser output power while the lasing efficiency is decreasing. Also, the maximum output energy can be at least about 33% greater than prior designs. In addition, the circuit is capable of generating a series of laser sub-pulses, each with approximately equal energies. Also, the number of sub-pulses, the delay between sub-pulses and the energy and peak power of each the sub-pulses can be independently adjusted and/or preprogrammed to achieve a predetermined pattern of sub-pulses. These capabilities are highly desirable in flashlamp excited medical lasers when pulses longer than those that can be efficiently generated are needed.

When flashlamps are driven by capacitor discharge circuits, these circuits typically generate a flashlamp pulse with decreasing light output intensity throughout the pulse. This is due to the decrease in voltage in the energy storage capacitor as it is being discharged during the pulse. The circuit of the invention can generate a constant or rising flashlamp pulse even as the voltage in the energy storage capacitor is decreasing. The circuit is capable of generating a series of flashlamp sub-pulses, within one capacitor charge-discharge cycle, such that the energy in each sub-pulses can be controlled individually using a feedback technique. This type of capability is very useful not only in laser excitation applications, but also in other applications where the output of a flashlamp needs to be advantageously controlled in time, such as in intense pulse light sources used for dermatological applications. In this case, the radiation of the flashlamp does not interact with a laser medium but instead directly irradiates the skin. A current sensor that measures the electrical current passing though the flashlamp can be used in place of the calibrated photodetector 23 to generate feedback signals comparable to the laser power signal 24 and the laser energy signal 25. The flashlamp can be housed in a handpiece including a reflector to reflect the light toward a window. The window can be used to transmit the light energy to the skin. The handpiece can also include circulating water to cool the flashlamp.

The invention has been described in terms of particular embodiments. The alternatives described herein are examples for illustration only and not to limit the alternatives in any way. The steps of the invention can be performed in a different order and still achieve desirable results. Other embodiments are within the scope of the following claims.

What is claimed:

1. An apparatus for driving a dermatological laser, the apparatus comprising:
    a first diode;
    an inductor, a first end of the inductor coupled to an electrode of the first diode, and a second end of the inductor coupled to a flashlamp adapted to generate one or more flashlamp light pulses, wherein the one or more flashlamp light pulses are received by a flashlamp-pumped laser to produce an output laser beam;
    a switch, an electrical control of the switch coupled to a control system, a first end of the switch coupled to a power source, a second end of the switch coupled to the first end of the inductor and the electrode of the first diode; and
    a photodetector adapted to i) measure output energy and output power of the laser beam produced by the flashlamp-pumped laser and ii) generate an output energy signal and an output power signal for transmission to the control system for modulating a flashlamp driving current to reach predetermined values of the measured output energy and output power.

2. The apparatus of claim 1 further comprising a second diode coupling the second end of the inductor to the flashlamp.

3. The apparatus of claim 1 further comprising a snubber circuit coupled to the first end of the inductor, the snubber circuit configured to supply a current to the inductor when the control system drives the electrical control to turn off the switch.

4. The apparatus of claim 1 wherein the flashlamp comprises one or more separate flashlamps connected in series.

5. The apparatus of claim 1 wherein the flashlamp-pumped laser is adapted to receive one or more flashlamp light pulses generated by the flashlamp for producing an output laser beam comprising one or more laser radiation pulses corresponding to the one or more flashlamp light pulses.

6. The apparatus of claim 1 wherein the control system is adapted to adjust an amplitude of the flashlamp driving current in coordination with a changing lasing efficiency of the flashlamp-pumped laser.

7. The apparatus of claim 1 wherein the flashlamp-pumped laser is a flashlamp-pumped dye laser, the flashlamp-pumped dye laser comprising a liquid dye laser medium adapted to receive one or more flashlamp light pulses generated by the flashlamp for producing an output laser beam comprising a laser treatment pulse, the laser treatment pulse comprising one or more laser radiation sub-pulses corresponding to the one or more flashlamp light pulses.

8. The apparatus of claim 7 wherein the laser treatment pulse is initiated by a trigger signal, and the trigger signal initiating an emission of the laser treatment pulse at a repetition rate up to about 2 pulses per second, each laser treatment pulse having an energy greater than about 1 Joule.

9. The apparatus of claim 7 wherein the laser treatment pulse comprises a single laser radiation sub-pulse of greater than 100 microseconds duration.

10. The apparatus of claim 9 wherein the single laser radiation sub-pulse is one of: substantially constant output power, rising output power, or decreasing output power.

11. The apparatus of claim 7 wherein the laser treatment pulse comprises between two and eight laser radiation sub-pulses each being at least about 10 microseconds duration, the laser treatment pulse being spaced out over a time of about 400 microseconds to about 40 milliseconds, the energy in each laser radiation sub-pulse being substantially equal.

12. The apparatus of claim 11 wherein each of the laser radiation sub-pulses are one of: substantially constant output power, rising output power, or decreasing output power.

13. The apparatus of claim 7 further comprising:
a wavelength sensor; and
a tuning system in communication with the wavelength sensor for varying a wavelength of the one or more laser radiation pulses.

14. The apparatus of claim 13 wherein the wavelength of the one or more laser radiation pulses is between about 580 nanometers to about 610 nanometers.

15. The apparatus of claim 13 wherein the wavelength of the one or more laser radiation pulses is between about 590 nanometers to about 600 nanometers.

16. The apparatus of claim 7 further comprising a flexible aiming device for directing the output beam to a treatment region.

17. The apparatus of claim 7 further comprising an aiming device for providing an aiming beam to align the output beam with a treatment region, the aiming beam comprising green light.

18. The apparatus of claim 7 further comprising a cryogen spray device for cooling a treatment region prior to irradiation.

19. The apparatus of claim 1 wherein the switch is an insulated gate bipolar transistor (IGBT) and the electrical control is a gate of the IGBT.

\* \* \* \* \*